United States Patent [19]

Wetterlin

[11] Patent Number: 4,524,769
[45] Date of Patent: Jun. 25, 1985

[54] DOSAGE INHALATOR

[75] Inventor: Kjell I. L. Wetterlin, S Sandby, Sweden

[73] Assignee: Aktiebolaget Draco, Lund, Sweden

[21] Appl. No.: 389,213

[22] Filed: Jun. 17, 1982

[30] Foreign Application Priority Data

Jul. 8, 1981 [SE] Sweden ................................ 8104239

[51] Int. Cl.³ ............................................. A61M 15/00
[52] U.S. Cl. ............................ 128/203.15; 128/203.12; 222/636
[58] Field of Search ........... 128/203.15, 200.4, 200.17, 128/203.12, 203.23, 204.13; 222/636, 345, 349

[56] References Cited

U.S. PATENT DOCUMENTS

| 11,485 | 4/1895 | Block | 222/349 X |
|---|---|---|---|
| 2,573,918 | 11/1951 | McCuiston | 128/200.17 |
| 2,581,182 | 1/1952 | Fields | 128/203.15 |
| 2,587,215 | 2/1952 | Priestly . | |
| 2,641,254 | 6/1953 | Brown | 128/203.23 |
| 3,653,380 | 4/1972 | Hansen . | |
| 3,658,059 | 4/1972 | Steil . | |
| 3,831,606 | 8/1974 | Danani | 128/203.15 |
| 4,003,500 | 1/1977 | Schornig | 222/636 X |
| 4,047,525 | 9/1977 | Kulessa et al. . | |
| 4,200,099 | 4/1980 | Guenzel et al. | 128/203.15 |
| 4,227,835 | 10/1980 | Nussbaum | 222/636 X |
| 4,253,591 | 3/1981 | Karihas | 222/636 |
| 4,262,666 | 4/1981 | Nelson | 128/203.23 |

FOREIGN PATENT DOCUMENTS

| 2704574 | 8/1977 | Fed. Rep. of Germany . | |
| 2837040 | 2/1980 | Fed. Rep. of Germany . | |
| 2447725 | 1/1980 | France . | |
| 81040016 | 6/1981 | Sweden . | |
| 2041763 | 9/1980 | United Kingdom . | |
| 570775 | 11/1970 | U.S.S.R. . | |
| 651766 | 11/1972 | U.S.S.R. . | |
| 799766 | 1/1981 | U.S.S.R. | 228/203.15 |

Primary Examiner—Edward M. Coven
Attorney, Agent, or Firm—Brumbaugh, Graves, Donohue & Raymond

[57] ABSTRACT

A powder inhalator which is activated by the air flow generated at inhalation and which is intended for inhalation of solid pharmacologically active compound in micronized form, said inhalator comprising a nozzle 2, an air conduit 6, a dosing unit 10 comprising a storage chamber 5 for the active compound and dosing means 8, and a maneuvering unit 1, characterized in that the dosing unit 10 comprises a storage chamber 5 for the active compound, a perforated membrane 4, a holder 9 for the said perforated membrane, and dosing means 8 for introducing active compound into the perforations in the perforated membrane 4, whereby means are arranged for displacing the membrane 4 in relation to the dosing means 8, whereby in a first position solid active compound in micronized form is introduced into the perforations in part of the area of the membrane 4 and in a second position the said part of the membrane 4 is inserted in the air conduit 6 for the air to be inhaled.

12 Claims, 3 Drawing Figures

DOSAGE INHALATOR

FIELD OF THE INVENTION

The present invention relates to a new dosage inhalator, intended to be activated using the air flow generated at inhalation and intended to be used for inhalation of pharmacologically active compound in solid, micronized form.

BACKGROUND OF THE INVENTION

Special requirements are made with regard to dosage inhalators intended for local administration of drugs to the respiratory tract and to the lungs. Since mostly very potent drugs are to be administered, the dose accuracy must be great. The dosage of active compound that is to be administered may be as small as 0.1 mg. It is also necessary that the particles that leave the dosage inhalator have a suitable size distribution, since too big particles tend to be deposited in the mouth. A typical formulation of isoproteranol sulfate powder intended for administration as an aerosol is described in the U.S. Pharmacopeia of July 1, 1980 as being sufficiently powdered that the great majority of individual particles are less than 5 $\mu$m in diameter. The British Pharmaceutical Codex of 1973 similarly discloses that in both ergotamine sulfate aerosols and isoprenaline sulfate aerosols most of the individual particles have a diameter of not more than 5 $\mu$m.

Several systems are available for local administration of drugs to the respiratory tract and to the lungs. Among these systems may be mentioned nebulizing devices, pressurized aerosols, pump inhalators, and inhalators which are activated by the air flow generated at inhalation, herebelow denoted "powder inhalators".

Several types of powder inhalators are available on the market. They represent a complement to pressurized aerosols, where the drug is dissolved or suspended in a liquid propellant mixture. The powder inhalators have the advantage that they always deliver the active compound when the patient inhales, as the particle cloud is generated by the air flow obtained at inhalation. Thereby the problem of coordinating the activation of a dosage with the inhalation in order to bring the active compound to the respiratory tract and to the lungs is solved. An example of powder inhalators which are available on the market is Spinhaler ®. In Spinhaler ® the active compound is used in micronized form, contained in a hard gelatine capsule which is perforated before use. The hard gelatine capsule is placed in a tube in a device which is brought to rotation by the air flow generated at inhalation, whereby the micronized compound is moved into the air stream and is brought via the air flow to the respiratory tract and lungs of the patient.

However, the previously known powder inhalators have disadvantages:

(1) they cannot be used for accurate and reproducible dispensing of micronized active compound in amounts below 15-20 mg, and they are therefore useful only for less potent active compounds or for highly potent active compounds in combination with a diluting agent, usually lactose;

(2) they are cumbersome to load and to make clean;

(3) usually several inhalations are required to empty a capsule containing a unit dose;

(4) they are difficult to handle for patients with reduced breathing capacity or with reduced capability in the use of their hands and;

(5) lactose, the diluting agent, is very disturbing at inhalation and may increase the frequency of caries.

There is a need for an effective powder inhalator which is activated by the air flow generated at inhalation, which is easy to handle for the patient, which allows dispensation of active compound in an amount down to 0.1 mg without need to include any diluting agent, and which gives a suitable size distribution for the particles which are administered.

The Invention

The present invention relates to a dosage inhalator, a so called "powder inhalator", which is activated by the air flow generated at inhalation, and which makes it possible to dispense solid active compound in micronized form, in a suitable size distribution, in an amount from 0.1 mg without need for any diluting agent. The dosage inhalator can be constructed for administering active compound in an amount up to 5 mg. It can also, with suitable construction of the dosing unit, be used for administering active compound in an amount of 5-50 mg.

The powder inhalator of the invention is activated by the air flow generated at inhalation and is intended for inhalation of solid pharmacologically active compound in micronized form. As is described in the appended claims, the powder inhalator comprises a nozzle, an air conduit, a dosing unit comprising a storage chamber for the active compound and dosing means for measuring the intended dosage of the active substance, and a maneuvering unit for operating the dosage unit. The powder inhalator is characterized in that the dosing unit comprises a storage chamber for the active compound in combination with dosing means comprising a perforated membrane, a holder for said perforated membrane, means for introducing active compound into the perforations in the perforated membrane, and means for displacing the membrane in relation to the storage chamber, whereby in a first position solid active compound in micronized form is introduced into the perforations in part of the area of the membrane and in a second position the said part area of the membrane is inserted in the conduit for the air to be inhaled.

The dosing means in combination with the storage chamber for the active compound represent the essential new elements in the powder inhalator according to the invention.

One embodiment of the dosage inhalator according to the invention is now described more in detail with reference to FIGS. 1, 2, and 3.

Figure 1:
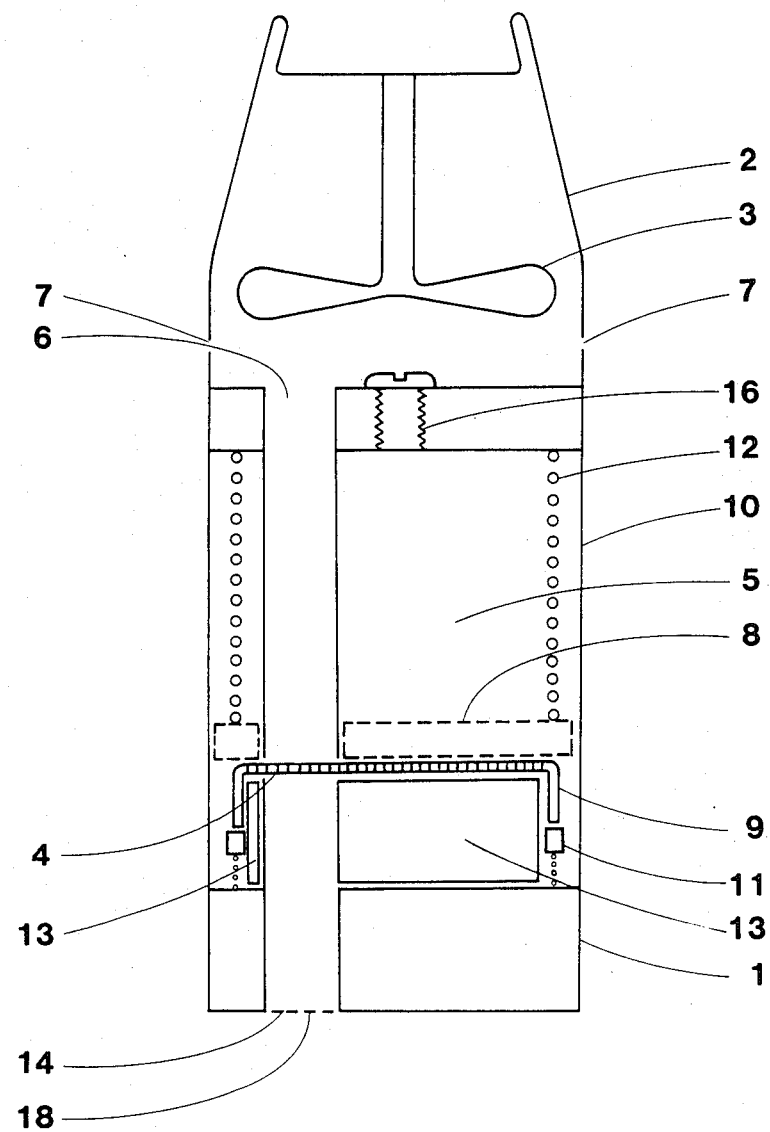
FIG. 1 is a sectional view through the dosage inhalator according to the invention.

The dosage inhalator comprises a maneuvering unit 1 which is used for feeding dosages of the active compound, a nozzle 2 which may be provided with rotating means 3 intended for disrupting such aggregate particles of the active compound which might have been formed, a dosing unit 10 for measuring the intended dosage of the active compound and a storage chamber 5 for solid micronized active compound.

The dosage inhalator also comprises an air conduit 6 intended for passage of the air to be inhaled. The nozzle 2 can be provided with rotating means 3 intended for disrupting such aggregate particles of the active compound which might have been formed. The disintegration of possible particle aggregates is facilitated by air inlets 7 arranged at the side of the nozzle 2.

The dosing unit 10 comprises a storage chamber 5 for the active compound a perforated membrane 4, a holder 9 for the perforated membrane, and dose loading means 8, schematically shown in FIG. 1, for introducing the active compound into the perforations in the perforated membrane 4. The dosing unit 10 and the perforated membrane 4 are displaceably arranged in relation to one another between a first position where active compound by the dose loading means 8 is introduced into the perforations in part of the area of the perforated membrane 4, and a second position where the said part area of the loaded membrane 4 has been inserted into the air conduit 6 in the dosage inhalator. In said first position of the membrane 4, the active compound is brought from the storage chamber 5 into the perforations in the membrane 4. When a part area of the membrane 4 containing such perforations filled with active compound thereafter is inserted into the air conduit 6, the active compound contained in the perforations will be entrained at inhalation and be brought through the nozzle 2 to the respiratory tract and the lungs of the patient.

The introduction of active compound into the perforations in the perforated membrane 4 is in the described embodiment made with mechanical means 8 consisting of elastic, spring-loaded scrapers 15, mounted in a holder 17 in the storage chamber 5. See FIGS. 2 and 3.

In a preferred embodiment, the perforated membrane 4 is displaceably arranged in relation to the storage chamber 5.

In another preferred embodiment, the dosing unit 10 comprises a perforated membrane 4 which can be rotated and which is intended to be loaded with solid active compound in micronized form.

In a further preferred embodiment, elastic spring-loaded scrapers 15 are arranged in the storage chamber 5 to introduce active compound into the perforations in the perforated membrane 4.

In another preferred embodiment, the perforations in the perforated membrane 4 are in the form of truncated cones with their large opening directed to the nozzle.

The scrapers 15 are suitably manufactured in an elastic material, for example rubber or plastic. The scrapers are suitably arranged so that when the active compound is introduced into the perforations in the membrane 4 they touch the surface of the membrane at an angle which is less than 90°. When the means for introducing active compound into the perforations in the membrane are arranged in this manner, the additional advantage is obtained that possible aggregates of active compound are disintegrated before administration.

The scrapers 15 are suitably arranged so that they press against the surface of the membrane 4. That is achieved as shown in FIG. 1 by having the scrapers 15 loaded by a spring 12. The spring 12 is arranged in the storage chamber 5 as is shown in FIG. 1.

Alternatively, a spring can be arranged so that the membrane 4 is pressed against the scrapers 15. The spring may in such case be arranged outside the storage chamber 5, suitably mounted in the maneuvering unit 1. Further variations are possible. The essential element is that the scrapers 15 press against the membrane 4 in such a way that active compound is introduced into the perforations in the membrane 4 when the maneuvering unit is operated. See FIG. 2 and FIG. 3.

In the maneuvering unit 1, immediately adjacent to the membrane 4, a plate 13 is arranged which prevents active compound from passing through the perforations in the membrane 4. See FIG. 1. Thus, the plate 13 will comprise the bottom of the perforations.

The air conduit 6 passes through the maneuvering unit 1. At inhalation through the nozzle 2 the air flow will pass partly through the air inlets 7 arranged at the side of the nozzle 2, and partly through the air conduit 6. The air in the air conduit 6 passes through its opening 14 in the maneuvering unit 1. In the embodiment shown in FIG. 1, a perforated plate 18 is arranged as a filter in the opening 14 in order to prevent undesired particles of larger size from entering the air conduit 6.

The perforated membrane 4 in the dosing unit 10 can be made, as is illustrated in FIG. 1 and in FIG. 3, as a horizontal membrane. But also other embodiments are possible, for example a membrane in the form of a drum where the active compound is filled into the perforations from a storage chamber which can be arranged outside the drum or inside the drum.

When a membrane in the form of a horizontal plane is used, as illustrated in FIG. 1, the membrane can be mounted so that it can be moved by rotating it, whereby the other parts of the dosage inhalator are fixed relative to one another.

In order to make sure that the amount of active compound that has been filled into the perforations which are inserted in the air conduit 6 is released from the perforations and entrained at inhalation, the said perforations in the membrane are suitably formed as truncated cones, see FIG. 3, with the wider opening directed towards the nozzle. Perforations in the form of truncated cones facilitate the emptying of the perforations in that the active compound is released more easily. Moreover, when the storage chamber 5 is arranged between the membrane and the nozzle, also the filling of the perforations is facilitated if the perforations are designed as is shown in FIG. 3.

The perforations in the perforated membranes can be of arbitrary design. They can be circular, square, elliptic, rectangular or have other geometrical form. The area of the perforations in the membrane can be a large or a small part of the membrane area, for example from 1 to 95%, whereby the term "membrane area" refers to that part of the area of the membrane which is inserted into the air conduit. The number of perforations in the membrane area can vary depending on factors such as the amount of active substance that is to be administered per dosage, the physical properties of the active substance, etc. In a preferred embodiment the perforations have a conical shape.

The perforated membrane can be manufactured in any suitable material, for example metal or plastic. The size of the dosage of active compound which is to be administered is determined by the size of the perforations in the membrane, the thickness of the membrane, the number of perforations in the membrane and by the size of the air conduit. A single perforation may be sufficient for dispensing a given dose of the active compound The accuracy of the dosage will mainly depend on the accuracy in the manufacturing of the membrane.

Examples of perforated membranes that can be used are the metal nets which are manufactured by Veco Beheer B.V., Eerbeek, The Netherlands. These nets can be obtained with various sizes of perforations. They can be formed in desired manner, for example in drum form or they can be used in the form of horizontal, plane membranes. Also woven nets of metal, fiber or of other materials can be used. The important factor is the dosage accuracy that can be obtained.

Figure 2:
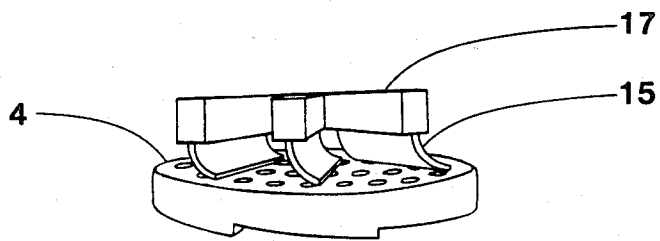
FIG. 2 shows scrapers in the storage chamber, which scrapers are used to introduce active compound into the perforations in the perforated membrane.
Figure 3:
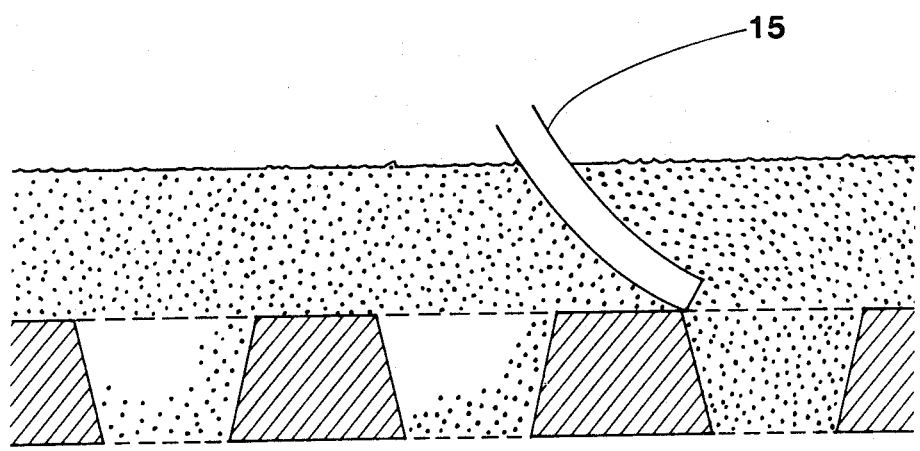
FIG. 3 shows how the active compound is fed from the storage unit into the perforations in the perforated membrane using the said scrapers.

The maneuvering unit 1 is in the embodiment shown in FIG. 1 arranged adjacent to the dosing unit 10. The maneuvering unit can be made in the form of a detent ring, as is shown by the ratcheted edge of membrane 4 in FIG. 2, where spring-loaded pins 11, see FIG. 1, are used to provide distinct positions for the perforated membrane when it is advanced by operating the maneuvering unit 1. The maneuvering unit can be arranged also otherwise, for example by arranging it to operate directly on the perforated membrane.

The storage chamber is in a preferred embodiment arranged between the perforated membrane and the nozzle. See FIG. 1.

The storage chamber can be arranged to accomodate a varying amount of the active compound. In a dosage inhalator where the storage chamber is not made for refilling of active compound it can contain an amount of active compound corresponding for example up to about 200 dosage units. In a dosage inhalator where the storage chamber is intended for refilling a device is required which can be arranged on the top or on the sides of the storage chamber. For example, a screw or plug 16 can be arranged in the storage chamber 5 as is shown in FIG. 1.

The air conduit 6 can have an area of 25-350 mm$^2$. The air conduit can be circular or have other geometrical form. If it is circular, the diameter may be from 3 to 10 mm.

Among compound groups and specific compounds which are suitable for administering with a powder inhalator according to the present invention the following can be mentioned betareceptorstimulating agents such as adrenaline, isoprenaline, orciprenaline, salbutamol and terbutaline, steroids for inhalation such as budesonide, and substances intended for nasal administration.

Especially useful are terbutaline and budesonide.

The active compound can be administered in micronized form without additional ingredients or in pharmaceutically modified micronized form in order to obtain improved flow properties. The micronized particles may be covered with a film functioning for example by masking bitter taste of the active compound, or by providing slow release of the active compound in the respiratory tract.

In an additional aspect, the present invention relates to the use of a perforated membrane as dosing means for solid micronized active compound in powder inhalators.

What we claim is:

1. A dosage inhalator for dispensing to a patient a micronized solid, pharmacologically active compound in dry powdered form having a particle size of less than 5 micrometers suspended in a gas, comprising:
   a nozzle;
   a conduit connected to the nozzle;
   a storage chamber adjacent said conduit for storing said active compound to be dispensed by said inhalator;
   a perforated membrane having a plurality of preselected perforated portions each holding and dispensing a reproducible unit dose of less than 50 mg. of said micronized compound, said membrane being mounted for movement between said conduit and said storage chamber so that one of said preselected portions is positioned across said conduit whereby the active compound held in the perforation thereof can be dispensed into the conduit and another of said preselected portions thereof is disposed within said storage chamber;
   dose loading means for introducing said active compound in the storage chamber into the perforation of the preselected portion of said membrane disposed within the storage chamber; and
   maneuvering means for displacing the perforated membrane through a plurality of positions whereby successive preselected portions of the perforated membrane holding the active compound are positioned across said conduit for dispensing the active compound.

2. A dosage inhalator according to claim 1, wherein the perforated membrane is mounted for rotation.

3. A dosage inhalator according to claim 2, wherein the dose loading means includes a scraper and a spring urging the scraper against the perforated membrane, the scraper and the spring being arranged in the storage chamber.

4. A dosage inhalator according to claim 2, wherein the dose loading means includes a scraper and the maneuvering means includes a spring urging the perforated membrane against the scraper.

5. A dosage inhalator according to claim 2, 3, or 4, wherein each perforation has a frustoconical shape with a larger end and a smaller end, the larger end being located closer to the nozzle.

6. A dosage inhalator according to claim 5 wherein each preselected portion of the membrane has a plurality of perforations of substantially the same size therein for holding and dispensing a share of the reproducible dose dispensed by said preselected portion.

7. A dosage inhalator according to claim 1, further comprising an active compound stored in the storage chamber, the active compound being terbutaline.

8. A dosage inhalator according to claim 1, further comprising an active compound stored in the storage chamber, the active compound being budesonide.

9. A dosage inhalator according to claim 1 wherein the unit dose of the active compound held and dispensed by each preselected perforated portion of the membrane is in the range of about 0.1 mg. to 5 mg.

10. A dosage inhaler for administering a micronized pharmacologically active substance to a patient comprising:
    a gas conduit means through which gas passes for carrying said micronized substance to be administered;
    a membrane having a plurality of preselected perforated portions each adapted to hold and dispense a reproducible unit dose of less than 50 mg of said active substance, in dry powder form, having a particle size of less than 5 micrometers, which membrane is movably connected to said gas conduit means so that one of said preselected portions can be positioned within said gas conduit means to dispense substance held in said preselected portion and the remaining preselected portion can be in a position external to said gas conduit means to receive said active substance, said membrane being movable through a plurality of positions whereby each preselected portion of the membrane can be successively positioned within said gas conduit to dispense the unit dose of the active substance held therein and whereby each preselected portion from which said active substance has been dispensed can be moved to said external position to receive active substance.

11. A dosage inhaler according to claim 10 wherein said portions of the perforated membrane are each adapted to hold and dispense a dose of said active substance in the range of about 0.1 mg. to 5 mg.

12. A dosage inhalator according to claim 10 wherein each of said preselected portions of the membrane has a plurality of perforations of substantially the same size therein, each such perforation being adapted to hold and dispense a share of the reproducible dose dispensed by said preselected portion.

* * * * *